United States Patent [19]

Holtkamp, Sr.

[11] Patent Number: Plant 6,111

[45] Date of Patent: Feb. 23, 1988

[54] AFRICAN VIOLET PLANT NAMED LAURIE

[75] Inventor: Reinhold Holtkamp, Sr., Isselburg, Fed. Rep. of Germany

[73] Assignee: Gessellschaftsvertrag uber die Erfindergemeinschaft "OPTIMARA", Rees Haffen, Fed. Rep. of Germany

[21] Appl. No.: 823,518

[22] Filed: Jan. 28, 1986

[51] Int. Cl.[4] ..... A01H 5/00

[52] U.S. Cl. ..... Plt./69

[58] Field of Search ..... Plt. 69

*Primary Examiner*—Robert E. Bagwill

*Attorney, Agent, or Firm*—Schwartz, Jeffery, Schwaab, Mack, Blumenthal & Evans

[57] ABSTRACT

An African violet plant named Laurie having purple-pink flower color which is a more intense purple in the center; very prominent and bright yellow anthers which create a very good contrast with the flower color; profuse flowering; vigorous growth habit and early flowering; and long-lasting, non-dropping flowers which form a tight flower head above the leaves.

1 Drawing Figure

The present invention comprises a new and distinct cultivar of African violet plant, botanically known as *Saintpaulia ionantha*, and hereinafter referred to by the cultivar name Laurie.

The new cultivar was originated from a cross made in a controlled breeding program in Isselburg, West Germany. The female, or seed parent was a cultivar designated C31/1 white blue. The male, or pollen parent was a cultivar designated D154/5 blue single. The new cultivar was given the breeding number H7312.

Laurie was discovered and selected by me as a flowering plant within the progeny of the stated cross in a controlled environment in Isselburg, West Germany. Asexual reproduction of the new cultivar by leaf cuttings, as performed by me at Isselburg, West Germany, has demonstrated that the combination of characteristics as herein disclosed for the new cultivar are firmly fixed and retained through successive generations of asexual reproduction.

Laurie has not been observed under all possible environmental conditions. The phenotype may vary significantly with variations in environment such as temperature, light intensity and day length. The following observations, measurements and values describe the new cultivar as grown in Isselburg, West Germany and Nashville, Tenn. under greenhouse conditions which closely approximate those generally used in commercial practice.

The following traits have been repeatedly observed and are determined to be basic characteristics of Laurie, which in combination distinguish this African violet as a new and distinct cultivar:

1. Star-shaped flower, with 5–7 anther cells forming a bright yellow center; the surface of the flower petal has a crystal-like sparkle.
2. Strong, upright, wire-like flower stems.
3. First flash of flowers form a tight bouquet free above the leaves.
4. Profuse flowering.
5. Long-lasting, non-dropping single flowers.
6. Each plant carries 7 to 9 and more upright flower stems, each of which carries 7 to 9 and more flowers; many additional lower buds appear in the petiole axle.
7. Plant saleable 8 to 9 weeks after potting.

8. The purple-pink color of the star-shaped flower intensifies towards the center to a dark purple-red, surrounding the yellow anther cells in the center.
9. Vigorous grower.
10. Seed capsule pushes slightly through.
11. After maturity the flowers dry off, and remain on the peduncle without becoming infected by botrytis.

The accompanying photographic drawing shows a typical specimen plant of the new cultivar grown in a 10 cm. pot. The colors appearing in the photograph are as true as possible with color illustrations of this type. Under cooler growing conditions or more intensive lighting, the purple-pink flower color intensifies.

In the following description, color references are made to The Royal Horticultural Society Colour Chart (R.H.S.), except where general colors of ordinary significance are referred to. Color values were taken under natural light conditions at approximately 1:00 p.m. in Nashville, Tenn.

Botanical classification: *Saintpaulia ionantha*, Ramat., cv. Laurie.

Parentage:

*Male parent.*—D154/5 blue single.

*Female parent.*—C31/1 white blue.

PROPAGATION

The new cultivar holds its distinguishing characteristics through successive propagations by leaf cuttings.

PLANT

From 9 cm. to 12 cm. tall when grown in pots, and approximately 24–27 cm. in diameter when fully grown.

Leaves:

*Shape.*—Generally heart-shaped, indented.

*Diameter.*—55–70 mm. wide.

*Texture.*—Velvety, slightly hairy.

*Ribs and veins.*—Under side well pronounced, light green and shiny; somewhat purple-green between the veins.

*Color (upper side).*—137A, with a tinge of brown.

*Color (under side).*—Light green; purple tinging between veins.

*Petioles.*—Strong and sturdy, hairy, brown-green in color.

Flowers:

*Buds.*—Size: 8–10 mm. before opening. Color: Greenish-brown.

*Sepals.*—Shape: Spear-shaped, hairy; five in number. Color: Greenish-brown.

*Calyx.*—Basifixed.

*Peduncle.*—Character: Strong, upright, hairy. Color: Greenish-brown.

Individual flowers:

*Size.*—40–44 mm. in diameter.

*Shape.*—Single, star-shaped, with 5–7 petals, slightly wavy at edges.

*Color (upper side).*—74C-D; more intensive purple in center.

*Color (under side).*—78C-D.

*Borne.*—Each flower stem carries 8 or more flowers on strong, upright peduncles.

Flowering habit: Flowers 8–9 weeks after potting; profuse flowering and vigorous growth habits form compact flower head positioned above leaves.

Reproductive organs:

*Stamens.*—5–7 in number.

*Anthers.*—5–7 with two anther cells.

*Filaments.*—6 mm., bright green.

*Styles.*—6 mm., light purple with light green base.

Roots: Normally developed, white when young, turning slightly brownish when older.

Disease resistance: Good.

I claim:

1. A new and distinct cultivar of African violet named Laurie, as illustrated and described, and particularly characterized by its purple-pink flower color which is a more intense purple in the center; very prominent and bright yellow anthers which create a very good contrast with the flower color; profuse flowering; vigorous growth habit and early flowering; and by its long-lasting, non-dropping flowers which form a tight flower head above the leaves.

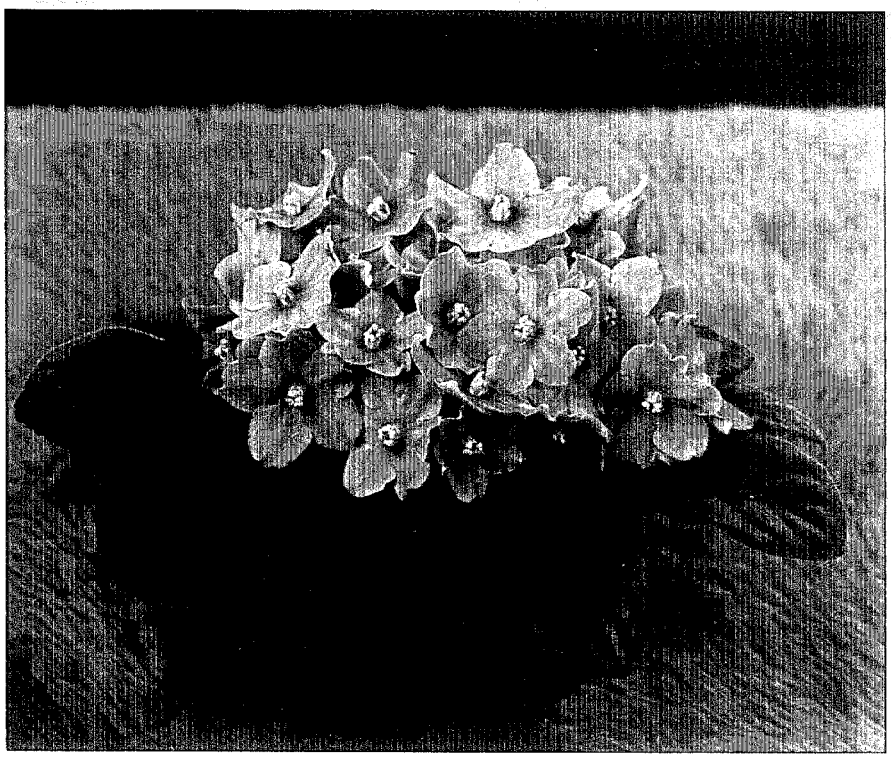

* * * * *